United States Patent [19]
Koester

[11] Patent Number: 5,349,398
[45] Date of Patent: Sep. 20, 1994

[54] OPHTHALMOMETER SYSTEM

[75] Inventor: Charles J. Koester, Glen Rock, N.J.

[73] Assignee: The Trustees of Columbia University in the City of New York, New York, N.Y.

[21] Appl. No.: 915,912

[22] Filed: Jul. 17, 1992

[51] Int. Cl.⁵ .............................................. A61B 3/10
[52] U.S. Cl. .................................. 351/212; 351/206; 351/221; 351/211; 359/350; 359/353
[58] Field of Search ................ 359/350, 353; 351/205, 351/206, 207, 210, 211, 212, 213, 221, 247; 128/745

[56] References Cited

U.S. PATENT DOCUMENTS

| | | | |
|---|---|---|---|
| 4,157,859 | 6/1979 | Terry | 351/13 |
| 4,208,107 | 6/1980 | Oharek | 351/221 |
| 4,355,871 | 10/1982 | Nevyas et al. | 351/13 |
| 4,407,572 | 10/1983 | Humphrey | 351/212 |
| 4,420,228 | 12/1983 | Humphrey | 351/212 |
| 4,540,254 | 9/1985 | Humphrey | 351/212 |
| 4,597,648 | 7/1986 | Feldon et al. | 351/212 |
| 4,662,730 | 5/1987 | Outwater et al. | 351/212 |
| 4,964,715 | 10/1990 | Richards | 351/212 |
| 5,042,939 | 8/1991 | Zayek | 351/205 |
| 5,058,596 | 10/1991 | Makino et al. | 128/745 |
| 5,141,303 | 8/1992 | Yamamoto et al. | 351/211 |

Primary Examiner—Loha Ben
Assistant Examiner—Thomas Robbins
Attorney, Agent, or Firm—John P. White

[57] ABSTRACT

An ophthalmometer system is provided which includes a white light source for illuminating a cornea during surgery, along with an infrared light generator for imaging concentric rings onto the cornea and a detection system for receiving the reflected infrared rings and providing them to a display to enable the surgeon to see the corneal topology as indicated by the nonconcentricity or concentricity of the reflected rings. The surgeon can thus view the cornea topology concurrently with surgical operations on the eye.

31 Claims, 1 Drawing Sheet

OPHTHALMOMETER SYSTEM

BACKGROUND OF THE INVENTION

The present invention is directed to an ophthalmometer system, and more particularly to an ophthalmometer or keratometer and surgical microscope system for making corneal measurements during eye surgery.

Ophthalmometers or keratometers are used to make various corneal topology measurements on the cornea. Various keratometers exist in the art, and are described in various U.S. patents including U.S. Pat. No. 4,157,859 to Terry, U.S. Pat. No. 4,355,871 to Nevyas et al., U.S. Pat. No. 4,407,572 to Humphrey, U.S. Pat. No. 4,540,254 to Humphrey, U.S. Pat. No. 4,597,648 to Feldon, U.S. Pat. No. 4,662,730 to Outwater and U.S. Pat. No. 4,964,715 to Richards.

For the most part, these keratometers require the surgeon to turn off microscope illumination of the cornea during surgery when the keratometer is to used. In some cases, the surgeon is further inconvenienced by having to insert a prism assembly when the keratometer is to be used. Then the procedures must be reversed if the surgeon wants to go back to regular illumination of the cornea for surgical operations.

SUMMARY OF THE INVENTION

It is an object of the present invention to provide an ophthalmometer system=which can perform corneal measurements during a surgical procedure such as cataract removal. For example, when a surgeon has to adjust tension in the sutures following a cataract removal operation, the present invention can be used to obtain corneal curvature measurements during corneal surgery. This is important because adjusting the tension in the sutures determines how free from astigmatism the cornea will be following the surgery.

In accordance with one aspect of the present invention, a corneal measuring system is provided having a light source and detector which utilize light having a different characteristic of than light which is utilized in the surgical illumination. For example, an infrared sensitive video camera can be used with an infrared optical system for measuring the cornea, while visible light with the infrared removed can be used for the surgical illumination. This allows the corneal curvature determination to be done simultaneously with the surgical procedure without the surgeon having to go back and forth between corneal measuring procedures and surgical procedures.

The present invention provides an optical system for illuminating the cornea during surgery and for measuring corneal topography, comprising first means for illuminating the cornea with first component light that is visible to a surgeon, second means for illuminating the cornea with second component light having a least one characteristic different from the first component light, and third means for directing the second component wavelength light to a corneal topography measuring apparatus while excluding said first component light. In accordance with another aspect of the present invention, an optical system for illuminating the cornea during surgery and for measuring corneal topography is provided. The system comprises first means for illuminating the cornea with light having at least a first wavelength component in the visible spectrum and second means for illuminating the cornea with light having a second wavelength different from the first wavelength component in the visible spectrum. Filtering means are provided for transmitting first wavelength component light to illuminate the cornea while excluding second wavelength light, and for providing first wavelength component reflected light for viewing the cornea during a surgical operation. Means are provided for directing second component wavelength light reflected off the cornea to a corneal topography imaging apparatus while excluding said first component wavelength light, said apparatus having means for displaying corneal topography information in response to the second component wavelength light, to thereby provide sufficient light of first wavelength to illuminate the cornea for and during surgical operations, while enabling corneal topography and curvature information to be displayed concurrently with corneal illumination.

Other objects and advantages of the present invention will be more readily apparent in considering the following detailed description of the invention, accompanying claims and attached drawing.

DETAILED DESCRIPTION OF THE PREFERRED EMBODIMENT

Figure 1:
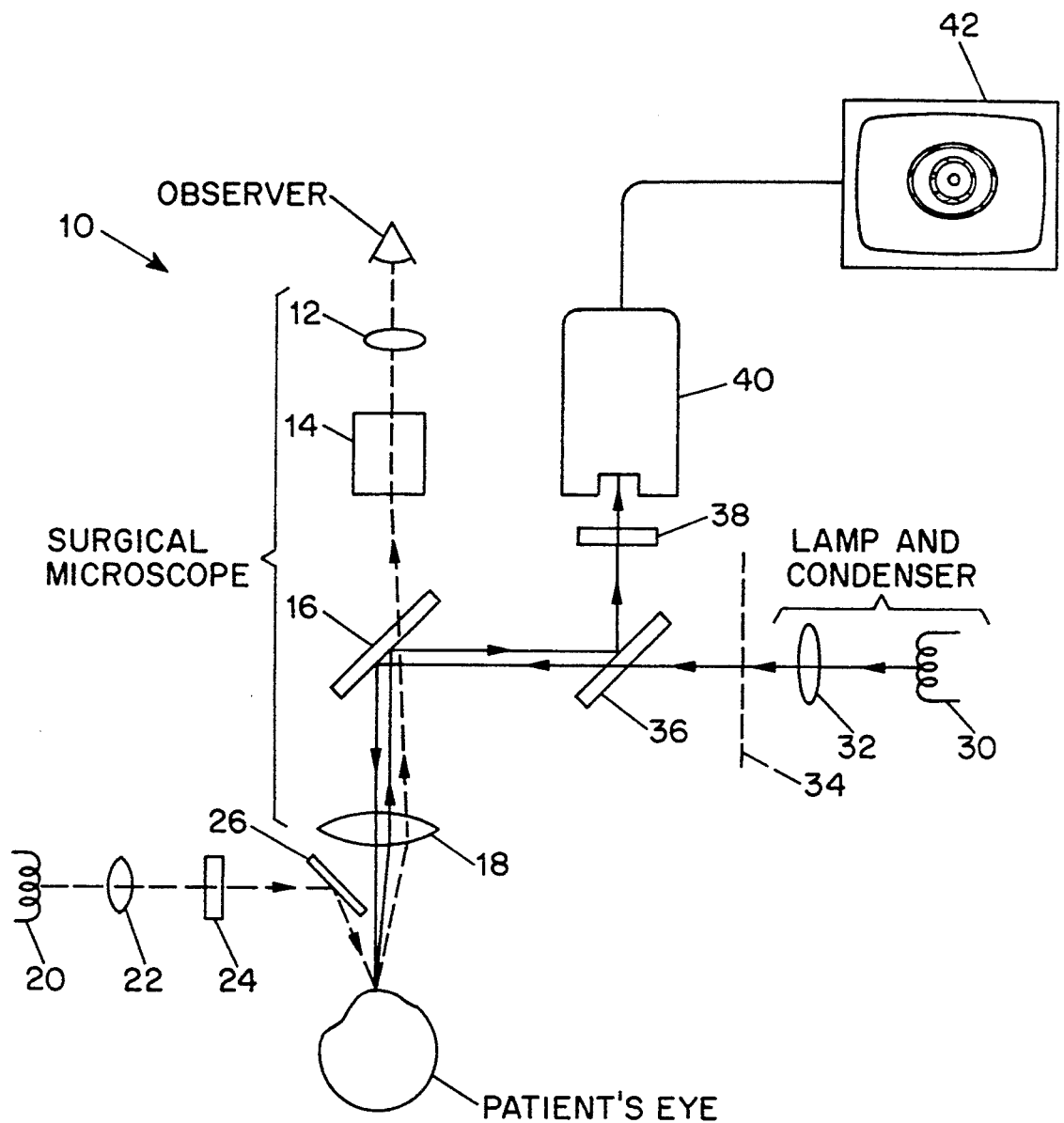
FIG. 1 is an side view of an ophthalmometer system implementation according to the present invention.

According to one aspect of the invention, an optical system for illuminating the cornea during surgery and for measuring corneal topography is provided, comprising first means for illuminating the cornea with first component light that is visible to a surgeon, second means for illuminating the cornea with second component light having a least one characteristic different from the first component light, and third means for directing the second component wavelength light to a corneal topography measuring apparatus while excluding said first component light.

The first means for illuminating may comprise a white light source, or a source of white light having a band of wavelengths missing. The light source may be chopped preferably at a frequency greater than about 60 Hz or the white light source may be substantially continuous.

The second means for illuminating may comprise an infrared light source, such as a light emitting diode.

When the first means for illuminating comprises a source of white light having a band of wavelengths missing, the second means for illuminating may comprise a light source having said band of wavelengths.

The second means for illuminating may comprise a laser, or a light source chopped at a different frequency than said white light source (when the white light is chopped).

The second means for illuminating may comprise a light source having an output which varies over time, and may be chopped or modulated. (The first means need not produce chopped or modulated light in this case.) The third means may comprise a cold mirror, an infrared transmitting filter, or a camera sensitive only to infrared light.

The third means may comprise filter/mirror means passing only the band of wavelengths, when the first means comprises a source of light having said band of wavelengths missing, and the second means comprises a light source having said band of wavelengths.

The third means may comprise a chopper which passes only light from said second means or a detector responding only to the second means.

In accordance with another aspect of the present invention, an optical system for illuminating the corneal during surgery and for measuring corneal topography is provided. The system comprises first means for illuminating the cornea with light having at least a first wavelength component in the visible spectrum, and second means for illuminating the cornea with light having a second wavelength different from the first wavelength component in the visible spectrum. Means are provided for providing first wavelength component reflected light for viewing the cornea during a surgical operation. Means are provided for directing second component wavelength light to the cornea, and to receive the second component light reflected off the cornea to a corneal topography imaging apparatus while excluding said first component wavelength light, said apparatus having means for displaying corneal topography information in response to the second component wavelength light, to thereby provide sufficient first wavelength light to illuminate the cornea for and during surgical operations, while enabling corneal topography and curvature information to be displayed concurrently with corneal illumination.

The first means for illuminating preferably comprises a white light source, and the first means for illuminating further may include a lens system for providing a magnified image of the eye.

The second means for illuminating preferably comprises an infrared light source, and reticle means for generating a ringed pattern to illuminate the cornea.

The first means for illuminating and the second means for illuminating preferably generate light which is incident the cornea generally along coincident paths substantially along the central axis of the cornea.

The filtering means preferably comprises a mirror means for transmitting first wavelength component light and for reflecting second wavelength component light. The mirror means is preferably a so-called "hot mirror" and wherein the first wavelength component light is white light and the second wavelength component light is infrared light.

The corneal topography imaging apparatus preferably comprises a video camera having a second filtering means for transmitting second wavelength component light while excluding first component wavelength component light and a video monitor connected to the camera for generating a display. The corneal topography imaging apparatus preferably displays information indicating the sphericity of the cornea.

In accordance with the present invention as shown in FIG. 1, an ophthalmometer system 10 is shown comprising an eyepiece 12, erecting prisms 14, a hot mirror 16 and a microscope objective 18. The elements 10, 12, 14 and 16 are typically provided in a surgical microscope.

Also shown in FIG. 1 is white light source 20 which emits full spectrum white light. The light source can be a tungsten illuminator. The light source emits white light, one representative ray being shown by a dotted line which passes through an objective lens 22 and a hot mirror 24. As those skilled in the art will understand, a hot mirror is a mirror that reflects infrared and transmits visible light.

The white light is then reflected downward towards a patient's eye by mirror 26. The white light beam impinges on the eye and is reflected off the eye where it travels upward through the microscope objective 18, through the hot mirror 16 because it is white light, through the erecting prisms 14, to eyepiece 12 where it can be seen by an observer. By this arrangement the observer can observe detail in the cornea during a surgical operation.

Shown on the right side of FIG. 1 is a detection system forming part of the present invention. The detection system comprises an infrared light source 30 and an objective lens 32. The infrared light source emits infrared light having a wavelength or wavelengths that may be in the 700–900 nm range, one representative ray of which is shown as the solid line in FIG. 1. The representative ray is directed towards reticle 34, passing through beam splitter 36 and toward the hot mirror 16.

The reticle 34 is a mask of concentric rings or circles of known diameters. Because the infrared light is reflected off the hot mirror, it travels downward through the microscope objective 18 to the patient's eye, and the concentric rings are projected onto the surface of the eye. The infrared light is then reflected off the patient's eye, through microscope objective 18 and is then reflected off hot mirror 16. The infrared light then is reflected off beam splitter 36 and passes through cold mirror 38.

As those skilled in the art will understand, a cold mirror is the substantial complement of a hot mirror in that it transmits infrared light therethrough, while reflecting white visible light. In this way it acts like a filter allowing light having a wavelength of greater than a certain cutoff wavelength, in this case about 700 nm, to pass through.

The infrared light then impinges on video camera 40, which may be a Sony AVC 1450 video camera or may be a CCD-type video camera. The video camera provides an image to monitor 42 which can be studied. Alternatively or additionally, the video camera may send the image to a computer, which in turn may analyze the image and present information to the surgeon in a number of different forms, e.g. (1) a video display of corneal contour, (2) a digital readout of spherical curvature, astigmatism, asphericity, etc., and/or (3) suggested surgical steps to correct the observed errors in corneal shape. Any departure from circular symmetry in the reflected ring patterns will indicate a departure from sphericity in the corneal surface and the observer, typically a surgeon, can make adjustments in the sutures to correct the asphericity.

The monitor 42 can thus provide an indication to the surgeon of the corneal topography of the patient's eye during a surgical operation. By having a white light source illuminate the eye to enable the surgeon to directly see the eye during a surgical operation, while infrared wavelength light performs a detecting function, both surgical illumination and keratometer observation can be carried on simultaneously.

The reticle may comprise one, two, or more rings as desired. If only one or two rings are used, the requirement for using a high numerical aperture (NA) lens near the eye is obviated. The reticle may be implemented using a Kodalith photographic material, available from Kodak.

The beam splitter 36 may be a beam splitter bearing trade designation ES30,725 and the hot mirrors are commercially available from Melles Griot bearing Model Nos. MG03MHG007 or 03MHG009 (for 45° degrees angle of incidence). These hot mirrors may be 25 mm in diameter. The cold mirror 38 may be a dielectric coated mirror, or may also be an infrared or IR Filter bearing trade designation RG 715 and having a thickness of 3 mm. It may also be a filter bearing trade designation RG 9 or other type of IR transmitting material as will occur to those skilled in the art.

The performance of hot mirror 24 and cold mirror 38 should be related. The hot mirror 24 should pass no light wavelengths that are transmitted by cold mirror 38. The cold mirror 38 could be replaced by a sharp cut-off filter that passes only wavelengths longer than the cut-off wavelength of hot mirror 24. The hot mirror 24 and cold mirror 38 should Be selected so that when they are placed in stacked configuration they together block all wavelengths of light. This will assure that none of the light from source 20 can reach the video camera 40. Of course, a video camera that has no sensitivity to wavelengths shorter than, say, 700 nm, would not require cold mirror 38.

When using the system in a surgical operation, stray infrared room light may cause a minor problem, so it may be necessary or desirable to cover any room lights with IR absorbing material. If stray IR room light still causes a problem, a specific infrared wavelength could be used, such as one having a wavelength of 760 nm. Then a narrow band filter would be used in front of the video camera instead of the cold mirror.

Other procedures could be employed to improve the signal-to-stray light ratio in the video camera. For example, camera circuitry could be designed to ignore constant DC light and respond only to chopped light at a particular frequency. Then the light for the keratometer can chopped at a frequency appropriate for the video camera. Steady illumination, from room lights, would be ignored. This arrangement could eliminate the need for hot mirror 24 and cold mirror 38. Alternatively, different frequencies could be used, for the surgical illumination 20 and keratometer illumination 30.

The invention thus contemplates a number of different combinations of first light sources and second light sources, along with respective means associated with the topography measuring apparatus for directing second component light to the apparatus while excluding first component light. One such combination could be white light for the first means, infrared light for the second means, and a cold mirror or infrared transfer filter for the third means. Another combination could be white light for the first means, infrared light for the second means, and a camera sensitive only to infrared light for the third means. Another combination could be white light with a band of wavelengths missing for the first means, light containing the band of wavelengths for the second means (this light could be generated by a laser), and for the third means a filter or mirror passing only the band. Another such combination could be white light which is chopped at a frequency of greater than 60 Hz, for example, the second means could be light chopped either out of phase with or at a different frequency than the first means and the third means could be a chopper which passes only light from the second means. By having the first and second means modulated at different frequencies, frequency sensitive detecting circuits may used to discriminate between the different frequency signals. This arrangement would also avoid the need to synchronize choppers. A yet further combination could be a steady white light source for the first means, chopped or modulated light for the second means, and for the third means a detector that responds only to the chopped or modulated light.

While one embodiment of the invention has been shown and described, numerous variations and modifications will readily occur to those skilled in the art. Such variations and modifications are intended to be within the scope of the present invention, which is defined in the appended claims.

We claim:

1. An optical system for illuminating the cornea during surgery and for measuring corneal topography, comprising:
   first means for illuminating the cornea with first component light that is visible to a surgeon;
   second means for illuminating the cornea with second component light having at least one characteristic different from the first component light, wherein the second means for illuminating includes a reticle means for generating a ringed pattern to illuminate the cornea; and
   third means for directing the second component light to a corneal topography measuring apparatus while excluding said first component light.

2. The optical system according to claim 1, wherein the first means for illuminating comprises a white light source.

3. The optical system according to claim 1, wherein the second means for illuminating comprises an infrared light source.

4. The optical system according to claim 1, wherein the third means comprises a cold mirror.

5. The optical system according to claim 1, wherein the third means comprises an infrared transmitting filter.

6. An optical system for illuminating the cornea during surgery and for measuring corneal topography, comprising:
   first means for illuminating the cornea with first component light that is visible to a surgeon;
   second means for illuminating the cornea with second component light having at least one characteristic different from the first component light; and
   third means for directing the second component light to a corneal topography measuring apparatus while excluding said first component light;
   wherein the first means for illuminating comprises a source of white light having a band of wavelengths missing.

7. The optical system according to claim 6, wherein the second means for illuminating comprises a source having said band of wavelengths.

8. The optical system according to claim 7, wherein said second means for illuminating comprises a laser.

9. The optical system according to claim 7, wherein the second means for illuminating comprises a light emitting diode.

10. The optical system according to claim 7, wherein the third means comprises filter/mirror means passing only the band of wavelengths.

11. An optical system for illuminating the cornea during surgery and for measuring corneal topography, comprising:
   first means for illuminating the cornea with first component light that is visible to a surgeon;
   second means for illuminating the cornea with second component light having at least one characteristic different from the first component light; and third means for directing the second component light to a corneal topography measuring apparatus while excluding said first component light;

wherein the first means for illuminating comprises a white light source and wherein the second component light is chopped.

12. The optical system according to claim 11, wherein the second component light is chopped at a frequency greater than about 60 Hz.

13. The optical system according to claim 11, wherein said second means for illuminating comprises a light source chopped out of phase with said white light source.

14. The optical system according to claim 13, wherein the third means comprises a chopper which passes only light from said second means.

15. The optical system according to claim 11, wherein said second means for illuminating comprises a light source chopped at a different frequency than said white light source.

16. An optical system for illuminating the cornea during surgery and for measuring corneal topography, comprising:

first means for illuminating the cornea with first component light that is visible to a surgeon;

second means for illuminating the cornea with second component light having at least one characteristic different from the first component light; and third means for directing the second component light to a corneal topography measuring apparatus while excluding said first component light;

wherein the first means for illuminating comprises a white light source and wherein the white light source is substantially continuous.

17. The optical system according to claim 16, wherein said second means for illuminating comprises a light source having an output which varies over time.

18. The optical system according to claim 17, wherein said second means for illuminating comprises a light source which is chopped.

19. The optical system according to claim 17, wherein said second means for illuminating comprises a modulated light source.

20. The optical system according to claim 17, wherein the third means comprises a detector responding only to the second means.

21. An optical system for illuminating the cornea during surgery and for measuring corneal topography, comprising:

first means for illuminating the cornea with first component light that is visible to a surgeon;

second means for illuminating the cornea with second component light having at least one characteristic different from the first component light and including infrared light; and third means for directing the second component light to a corneal topography measuring apparatus while excluding said first component light;

wherein the third means comprises a camera sensitive only to infrared light.

22. An optical system for illuminating the cornea during surgery and for measuring corneal topography, comprising:

first means for illuminating the cornea with light having at least a first wavelength component in the visible spectrum;

second means for illuminating the cornea with light having a second wavelength different from the first wavelength component;

third means for providing first wavelength component light reflected for viewing the cornea during a surgical operation; and fourth means for directing second component wavelength light reflected off the cornea to a corneal topography imaging apparatus while excluding said first component wavelength light, said apparatus having means for displaying corneal topography information in response to the second component wavelength light, to thereby provide sufficient light to illuminate the cornea for and during surgical operations, while enabling corneal topography and curvature information to be displayed concurrently with corneal illumination;

wherein the second means for illuminating includes a reticle means for generating a ringed pattern to illuminate the cornea.

23. The optical system according to claim 22, wherein the first means for illuminating comprises a white light source.

24. The optical system according to claim 22, wherein the first means for illuminating further includes a lens system for magnifying the cornea.

25. The optical system according to claim 22, wherein the second means for illuminating comprises an infrared light source.

26. The optical system according to claim 22, wherein the first means for illuminating and the second means for illuminating generate light which is incident the cornea generally along coincident paths substantially along the central axis of the cornea.

27. The optical system according to claim 22, further including a corneal topography imaging apparatus comprises a video camera having a second filtering means for transmitting second wavelength component light while excluding first component wavelength component light and a video monitor connected to the camera for generating a display.

28. An optical system for illuminating the cornea during surgery and for measuring corneal topography, comprising:

first means for illuminating the cornea with light having at least a first wavelength component in the visible spectrum;

second means for illuminating the cornea with light having a second wavelength different from the first wavelength component;

third means for providing first wavelength component light reflected for viewing the cornea during a surgical operation; and fourth means for directing second component wavelength light reflected off the cornea to a corneal topography imaging apparatus while excluding said first component wavelength light, said apparatus having means for displaying corneal topography information in response to the second component wavelength light, to thereby provide sufficient light to illuminate the cornea for and during surgical operations, while enabling corneal topography and curvature information to be displayed concurrently with corneal illumination;

wherein the third means comprises filtering means for transmitting first wavelength component light reflected off the cornea while reflecting second wavelength component light.

29. The optical system according to claim 28, wherein the filtering means comprises a mirror means for transmitting first wavelength component light and for reflecting second wavelength component light.

30. An optical system for illuminating the cornea during surgery and for measuring corneal topography, comprising:

first means for illuminating the cornea with light having at least a first wavelength component in the visible spectrum;

second means for illuminating the cornea with light having a second wavelength component different from the first wavelength component;

third means for providing first wavelength component light reflected for viewing the cornea during a surgical operation;

fourth means for directing second component wavelength light reflected off the cornea to a corneal topography imaging apparatus while excluding said first component wavelength light, said apparatus having means for displaying corneal topography information in response to the second component wavelength light, to thereby provide sufficient light to illuminate the cornea for and during surgical operations, while enabling corneal topography and curvature information to be displayed concurrently with corneal illumination; and a hot mirror for combining the first and second wavelength component light, wherein the first wavelength component light is white light and the second wavelength light is infrared light; and wherein the first means for illuminating and the second means for illuminating generate light which is incident on the cornea generally along coincident paths substantially along the central axis of the cornea.

31. An optical system for illuminating the cornea during surgery and for measuring corneal topography, comprising:

first means for illuminating the cornea with light having at least a first wavelength component in the visible spectrum;

second means for illuminating the cornea with light having a second wavelength different from the first wavelength component;

third means for providing first wavelength component light reflected for viewing the cornea during a surgical operation; and fourth means for directing second component wavelength light reflected off the cornea to a corneal topography imaging apparatus while excluding said first component wavelength light, said apparatus having means for displaying corneal topography information in response to the second component wavelength light, to thereby provide sufficient light to illuminate the cornea for and during surgical operations, while enabling corneal topography and curvature information to be displayed concurrently with corneal illumination, and wherein the corneal topography imaging apparatus displays information indicating the sphericity of the cornea.

* * * * *